(12) United States Patent
Somphone et al.

(10) Patent No.: US 11,712,225 B2
(45) Date of Patent: Aug. 1, 2023

(54) STABILIZATION OF ULTRASOUND IMAGES

(71) Applicant: KONINKLIJKE PHILIPS N.V., Eindhoven (NL)

(72) Inventors: Oudom Somphone, Paris (FR); Cecile Dufour, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/329,458

(22) PCT Filed: Sep. 5, 2017

(86) PCT No.: PCT/EP2017/072140
§ 371 (c)(1),
(2) Date: Feb. 28, 2019

(87) PCT Pub. No.: WO2018/046455
PCT Pub. Date: Mar. 15, 2018

(65) Prior Publication Data
US 2019/0216439 A1    Jul. 18, 2019

(30) Foreign Application Priority Data
Sep. 9, 2016   (EP) .................... 16306127

(51) Int. Cl.
*A61B 8/08*   (2006.01)
*G01S 15/89*   (2006.01)
(Continued)

(52) U.S. Cl.
CPC ............ *A61B 8/5276* (2013.01); *A61B 8/461* (2013.01); *A61B 8/469* (2013.01); *A61B 8/483* (2013.01);
(Continued)

(58) Field of Classification Search
CPC ..... A61B 8/5276; A61B 8/5246; A61B 8/461; A61B 8/469; A61B 8/483; A61B 8/5253;
(Continued)

(56) References Cited

U.S. PATENT DOCUMENTS 5,575,286 A   11/1996   Weng et al.
5,782,766 A   7/1998   Weng et al.
(Continued)

FOREIGN PATENT DOCUMENTS

WO   03047433 A2   6/2003

OTHER PUBLICATIONS

International Search Report and Written Opinion for International Application No. PCT/EP2017/072140, dated Nov. 22, 2017, 18 pages.
(Continued)

*Primary Examiner* — Peter Luong

(57) ABSTRACT

The invention provides a method of stabilising an ultrasound image, the method comprising generating a composite image of a current image and at least one previous image. The composite image has a region of interest which is stabilised based on at least obtained stabilisation information. Use of a current image and at least one previous image allows a composite image of a larger size to be produced.

16 Claims, 8 Drawing Sheets

(51) Int. Cl.
*G01S 7/52* (2006.01)
*A61B 8/00* (2006.01)

(52) U.S. Cl.
CPC .......... *A61B 8/5246* (2013.01); *A61B 8/5253* (2013.01); *G01S 7/52063* (2013.01); *G01S 7/52065* (2013.01); *G01S 7/52074* (2013.01); *G01S 15/8993* (2013.01)

(58) Field of Classification Search
CPC ............. G01S 15/8993; G01S 7/52063; G01S 7/52065; G01S 7/52074
See application file for complete search history.

(56) References Cited

U.S. PATENT DOCUMENTS

| | | | |
|---|---|---|---|
| 5,899,861 A * | 5/1999 | Friemel | G01S 7/5205 600/443 |
| 6,159,152 A | 12/2000 | Sumanaweera et al. | |
| 6,162,174 A * | 12/2000 | Friemel | G01S 7/52026 600/447 |
| 6,416,477 B1 * | 7/2002 | Jago | G01S 7/52065 600/447 |
| 8,303,505 B2 * | 11/2012 | Webler | G06T 7/38 600/447 |
| 2005/0096538 A1 | 5/2005 | Chomas et al. | |
| 2006/0058651 A1 | 3/2006 | Chiao et al. | |
| 2006/0146377 A1 * | 7/2006 | Marshall | G06T 3/4038 358/486 |
| 2007/0255137 A1 | 11/2007 | Sui et al. | |
| 2011/0255762 A1 | 10/2011 | Deischinger et al. | |
| 2012/0150036 A1 * | 6/2012 | Buckton | G01S 7/52026 600/447 |
| 2018/0064409 A1 * | 3/2018 | Schmidt-Richberg | G06K 9/3233 |

OTHER PUBLICATIONS

Somphone, et al., "Fast Myocardial Motion and Strain Estimation in 3D Cardiac Ultrasound With Sparse Demons", 2013 IEEE 10th International Symposium on Biomedical Imaging: From Nano to Macro, San Francisco, CA, Apr. 7-11, 2013, pp. 1182-1185.

* cited by examiner

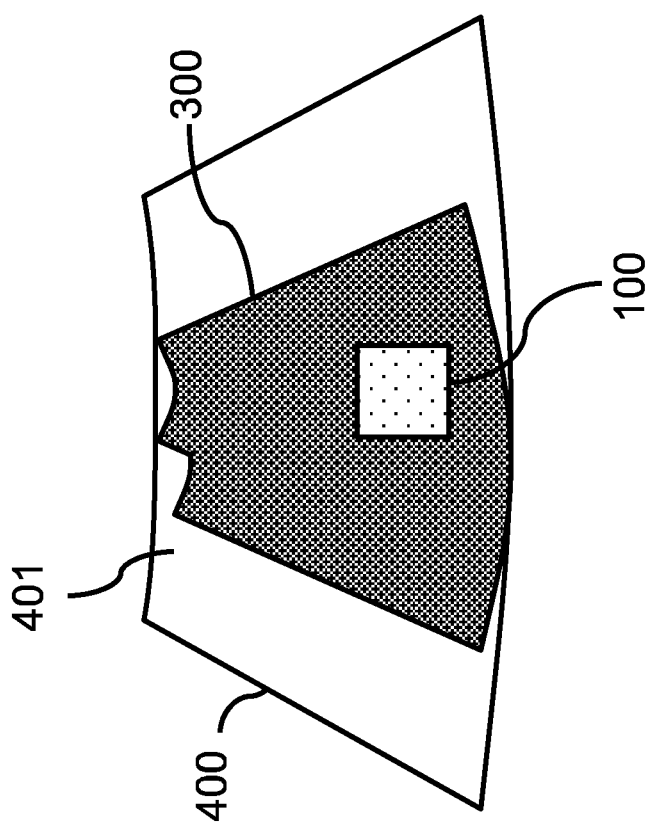

STABILIZATION OF ULTRASOUND IMAGES

FIELD OF THE INVENTION

This invention relates to the field of ultrasound imaging methods, and in particular, to methods of stabilising ultrasound images.

BACKGROUND OF THE INVENTION

Ultrasound imaging is often used in the medical industry for the purposes of diagnosis, and is particularly important in the field of urology and obstetrics. During a typical ultrasound imaging process, an ultrasound image is produced to show or identify a region of interest, such as a foetus or organ.

Typically, it is considered useful to stabilize the image with respect to the region of interest. In other words, images in an ultrasound sequence are often stabilised such that a user perceives the region of interest as substantially stationary and unmoving.

Such stabilisation is often performed to remove the global component of the motion (of the region of interest) in order to facilitate the visualization of any local deformation in the region of interest. Furthermore, stabilisation of a 3D image sequence may help to compensate for the out-of-plane motion that may occur in the cross-sections of an orthoviewer.

The inventors have recognised that there is a need to improve the visualisation of stabilized ultrasound sequences, in order to increase the clarity and ease of viewing the region of interest.

Document U.S. Pat. No. 5,575,286 discloses an image registration apparatus in which consecutive ultrasonic image frames are correlated in order to derive transducer motion information. A fast display technique generates compound images based on the derived global image motion.

Document US 2005/096538 discloses a medical imaging system that automatically acquires two-dimensional images representing a user-defined region of interest despite motion. The plane of acquisition is updated adaptively as a function of detected motion.

Document U.S. Pat. No. 5,782,766 discloses an image registration method for creating composite, panoramic images, in which a series of ultrasound image frames are correlated in order to derive transducer motion.

Document U.S. Pat. No. 6,159,152 discloses a method for registration of multiple ultrasound images, wherein the images are registered as a function of relative movement of the transducer. The images are registered and compounded to generate the panoramic field of view image as a function of the estimated motion.

Document WO 03/047433 discloses and ultrasonic diagnostic imaging system in which anatomical images are stabilized in the presence of probe motion, anatomical motion, or both.

SUMMARY OF THE INVENTION

The invention is defined by the claims.

According to a concept of the invention, there is provided an ultrasound imaging method for stabilising a region of interest, the method comprising: obtaining stabilization information for compensating motion of a region of interest in a sequence of ultrasound images, the sequence of ultrasound images comprising a current image and at least one previous image; and generating a composite image of the current image and the at least one previous image, the composite image comprising the region of interest, the region of interest being stabilized based on the stabilization information, wherein the composite image has predetermined dimensions, the predetermined dimensions being larger than the dimensions of at least the current image and, wherein: pixel values of the current image that fall within the field of view of the composite image are updated in the composite image; and pixel values of the current image that fall outside the field of view of the composite image are discarded.

There is proposed a concept of generating a composite ultrasound image having a stabilised region of interest based on a current (ultrasound) image and at least one previous (ultrasound) image.

As used herein, an image may be understood to be data representing an area or region imaged by an ultrasound system (e.g. comprising an ultrasound transducer array or ultrasound probe). A current image may be understood to be an image currently provided by the ultrasound system, and a previous image an image previously or earlier provided by the ultrasound system.

It is herein recognised that, when performing ultrasound imaging, a location of a region of interest (e.g. a foetus or organ) may move or change position for successive images. In a scenario in which a current image is stabilised with respect to the region of interest and a previous image, a field of view (e.g. the ultrasound image frustum) of the current image correspondingly changes from the field of view of the previous image. Thus, if each image, in a sequence of images of a moving region of interest, were to be stabilised, a sequence of images having different fields of view would be generated.

The proposed concept recognises that a composite image, having a stabilised region of interest, may be formed based on the current image and at least one previous image. By way of example, by compositing or splicing at least one previous image to the current image, a composite image may be generated.

Such a composite image has a stabilised region of interest; the stabilization being based on stabilisation information for compensating motion of the region of interest.

The stabilization information may, for example, be data representing a change in position, location and/or orientation of the region of interest within the sequence of ultrasound images.

It may be understood that the stabilisation information for compensating a motion of a region of interest is similarly representative of a change in the field of view of the image. For instance, before (or without) stabilization with respect to a region of interest, the region of interest moves and the field of view is fixed, whereas, after stabilization, the region of interest does not move (i.e. is stabilised) and the field of view moves. Such movement of the field of view (to stabilise the region of interest) may thus be thought of as describing (or being representative of) information that describes the movement of the region of interest, and therefore suitable for compensation motion of the region of interest.

The field of view of an image may, in embodiments, be understood to be representative of the dimensions, size, shape, position and/or orientation of the area associated with, mapped out by or shown by the image with respect to the region of interest. Put yet another way, the field of view of an image may define or represent at least one of a size, shape, position and/or orientation of a region imaged by an ultrasound system with respect to the region of interest.

By way of example, a first image in which a region of interest located toward an upper side of the image has a different field of view to a second image in which the region of interest is located towards a lower side of the image. In particular, the field of view of the first image reveals more of the area below the region of interest than the field of view of the second image.

By way of another example, a first and second image of a same size and orientation and in which a position and orientation of the region of interest is the same are associated with the same field of view.

In embodiments, the field of view of the composite image may be the union (i.e. combined or overall) field of view of the current image and the at least one previous image, such that the field of view of the composite image may be considered to be the total extent of the area or region imaged by an ultrasound system during imaging of the current image and at least one previous image with respect to the region of interest.

In preferable embodiments, the field of view of the composite image is predetermined, such that the dimensions of the composite image are predetermined.

Provision of a composite image having a stabilised region of interest may advantageously provide an image having borders which do not substantially move. This may increase the visibility of the region of interest. Furthermore, real-time generation of the composite image is enabled by use of only a current image and the at least one previous images.

In at least one embodiment, each ultrasound image is associated with a respective field of view, and the composite image may comprise, for areas outside the field of view of the current image, data from at least one previous image.

In other words, the composite image may comprise image data (e.g. pixel values) from at least one previous image to extend the field of view of the current image. Or, put another way, the composite image may have a larger field of view than that of the current image, wherein the portions of the composite image field of view which do not overlap with the current image field of view comprise data from at least one previous image.

By way of example only, the composite image may comprise the current image and identify areas or regions not included in the field of view of the current image, but present in the field(s) of view of the at least one previous images. Data from the at least one previous images may be used to extend the current image to include these identified regions, and thereby generate the composite image.

The generating of a composite image may comprise determining an overall field of view of the composite image based on the stabilisation information.

In other words, an overall or union field of view of the composite image may be determined based on the stabilisation information. As previously recognised, the stabilization information may correspond to the change in a field of view of the image. Thus, a field of view of the composite image may be determined based on the stabilisation information (as this may indicate e.g. a change in position of the field of view of the images in the image sequence).

Put yet another way, the field of view of the composite image may be a union of the fields of view of the current image and the at least one previous image. The field of view of the composite image thereby comprises the field of view of the current image and the field(s) of view of the at least one previous image.

The composite image may be generated by compositing the current image and portions of the at least one previous image until a full composite image is generated (i.e. having the determined field of view of the composite image).

Preferably, more temporally recent images are given priority over more temporally distant images. That is to say, in the event that images (in the image sequence) have an overlapping region, the more temporally recent image is used to fill that region of the composite image.

Optionally, generating the composite image comprises: stabilising the region of interest in the current image based on at least one previous image; and generating the composite image by compositing the stabilised current image with at least one previous image.

In other words, the method may comprise stabilising a current image (i.e. based on at least one previous image) and generating a composite image based on the stabilised current image and at least one previous image.

The method may further comprise processing image data of the current image and the at least one previous image in accordance with a smoothing algorithm.

By way of example, the method may comprise smoothing a boundary between the current image and portions of at least one previous image (i.e. in the composite image). In some embodiments, the composite image is processed in accordance with a smoothing algorithm so as to smooth a boundary between portions of the composite image associated with the current image and portions of the composite image associated with the at least one previous image.

The obtaining stabilisation information may comprise: determining a location of the region of interest in the current ultrasound image; determining a location of the region of interest in an immediately previous ultrasound image; and determining a change in location of the region of interest from the immediately previous ultrasound image to the current ultrasound image to generate stabilisation information.

Put another way, a method according to an embodiment may comprise determining how a position and/or size of a region of interest changes from one image to the next, and generating stabilisation information based on this determination. The stabilisation information may thereby comprise an indication of how a position and/or size of the region of interest changes throughout the sequence of ultrasound images. In particular, the stabilization information may comprise data indicating how the position of the region of interest changes from an immediately previous image to the current image.

Stabilisation of the region of interest may be performed based on this stabilization information. That is to say, by identifying how the region of interest moves or changes positions, it is possible to compensate for this motion.

By way of example, the stabilization information may comprise a vector indicative of a relative translation of the region of interest in the current ultrasound image with respect to an immediately previous ultrasound image.

In embodiments, the generating the composite, for example panoramic, ultrasound image is based on the current ultrasound image and no more than five previous ultrasound images.

The method may further comprise obtaining an identification of the region of interest in the current ultrasound image.

The identification of the region of interest may be performed by either receiving a user input indicative of a region of interest or performing a segmentation of image data of an ultrasound system.

In other words, in some embodiments, the method may be adapted to receive a user input indicating a region of interest.

Based on this indicated region of interest, the method may comprise obtaining stabilization information for stabilising the indicated region of interest (e.g. in at least the current image). By way of example, the method may comprise tracking a position of the indicated region of interest in past or previous images.

In other embodiments, the method may comprise performing a segmentation of image data received from an ultrasound system.

The region of interest may be tracked, based on surrounding image feature (e.g. borders or textures) using at least one predetermined algorithm.

In yet other examples, the identification of the region of interest is performed for an initial image (e.g. a first image in a sequence of images) and stabilization information may be generated tracking the motion of the identified region of interest (i.e. up to the current image).

The method may be a 3D ultrasound imaging method and the stabilisation information is for compensating a 3D motion of a region of interest in a sequence of 3D ultrasound images.

According to another embodiment of the inventive concept, there is provided an ultrasound imaging system comprising: an image stabiliser adapted to obtain stabilization information for compensating motion of a region of interest in a sequence of ultrasound images comprising a current image and at least one previous image; and an image generator adapted to generate a composite image of the current image and the at least one previous image, the composite image having a stabilized region of interest, wherein the stabilisation of the region of interest is based on the stabilization information, and wherein the composite image has predetermined dimensions, the predetermined dimensions being larger than the dimensions of at least the current image, and wherein: pixel values of the current image that fall within the field of view of the composite image are updated in the composite image; and pixel values of the current image that fall outside the field of view of the composite image are discarded. The ultrasound imaging system may further comprise a field of view obtaining system adapted to obtain data indicative of a field of view of each image in the image sequence.

The ultrasound imaging system may further comprise a region of interest identifier adapted to identify a region of interest in at least the current image.

In some embodiments, the at least one previous image may comprise a previous composite image having a stabilized region of interest. The image generator may therefore be adapted to generate a composite image of a previous composite image and the current image. In other words, the image generator may be updated to update a previously generated composite image with pixel data from one or more ultrasound images in an ultrasound sequence, the one or more ultrasound images being more temporally recent than the previously generated composite image.

An embodiment provides an ultrasound system, comprising: an ultrasound imaging system as previously described; and an ultrasound transducer array adapted to generate a sequence of ultrasound images.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which:

FIG. 4 illustrates a composite image generated based on the combined image;

DETAILED DESCRIPTION OF THE EMBODIMENTS

The invention provides a method of stabilising an ultrasound image, the method comprising generating a composite image having a stabilised region of interest based on a current image and at least one previous image. Use of a current image and at least one previous image allows a composite image of a larger size to be produced.

Illustrated embodiments are simply representative scenarios in which the inventive concept may be employed. Methods according to an inventive concept will be understood with reference to the Figures and the following description, which illustrate a number of scenarios for methods according to various embodiments.

During an ultrasound imaging process, an ultrasound system is adapted to sequentially take ultrasound images based on a data received from an ultrasound imaging acquisition device (such as an ultrasound probe or ultrasound imaging array). Typically, during such an imaging process, the ultrasound probe is maintained in substantially the same position. By way of example, an ultrasound probe may be positioned on a patient's stomach and held in position by a medical practitioner. However, a region or object of interest may move during the imaging process. The region of interest may be an object of interest, such as a foetus or organ, or a particular area or zone, such as a portion of an organ, a combination of more than one organ and so on.

Figure 1:
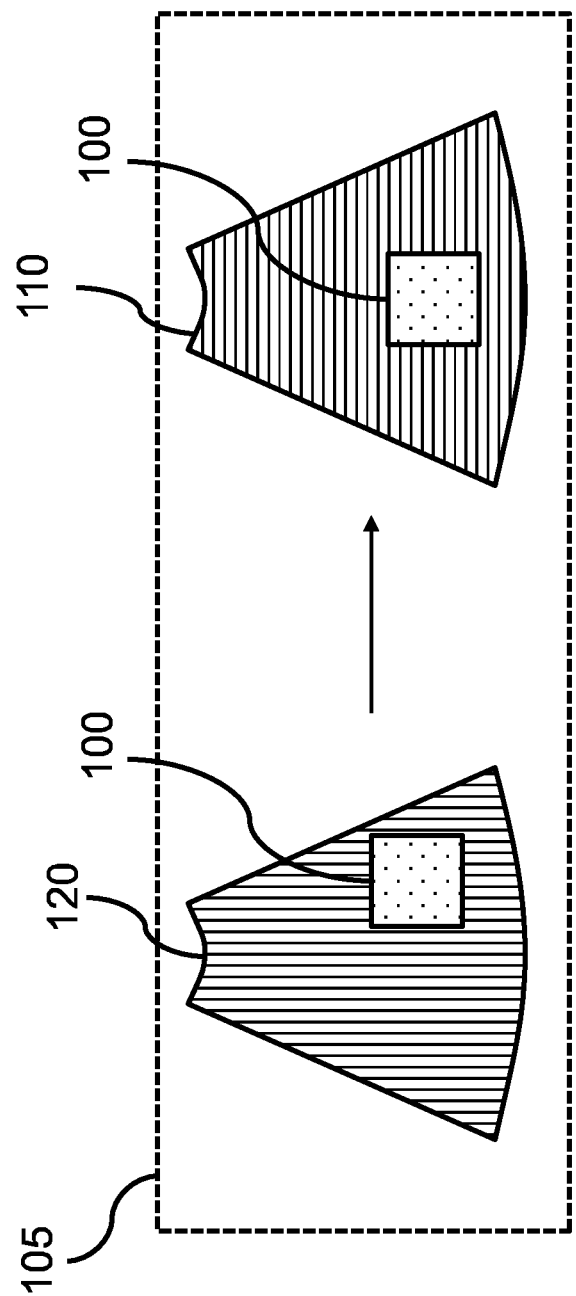
FIG. 1 illustrates a sequence of ultrasound images comprising a current image and a previous image.

Such a scenario is shown in FIG. 1, which illustrates a region of interest 100 which moves during an imaging process in which an ultrasound probe is maintained in substantially the same position.

In particular, FIG. 1 shows a simple sequence 105 of two ultrasound images comprising a current image 110 and a previous image 120. The position of the region of interest 100 in the current image 110 has moved with respect to the position of the region of interest 100 in the previous image 120. In other words, the region of interest has been translated.

To increase the clarity and reduce blurring of the region of interest (e.g. when displaying the images on a monitor), it may be preferable to stabilise the region of interest throughout the imaging process. Such a stabilisation process may be understood with reference to FIG. 2.

Figure 2:
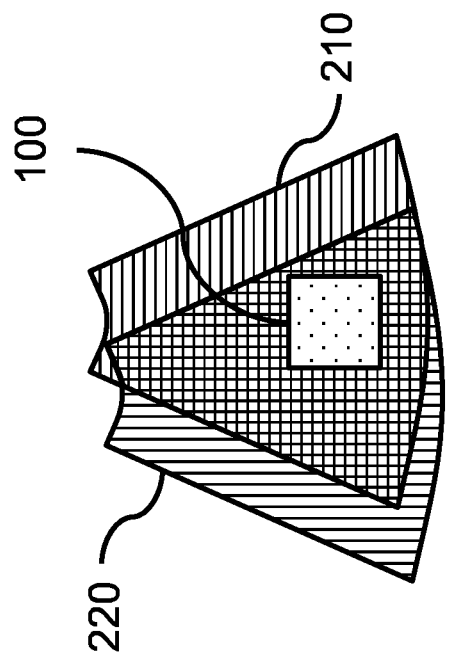
FIG. 2 illustrates a stabilised sequence of ultrasound images.

In particular, FIG. 2 shows a current image 210 and a previous image 220 which are stabilised with respect to one another, such that the region of interest is stabilised. The images are illustrated as overlaying one another to clearly show the stabilisation of the region of interest 100.

As the region of interest 100 is stabilised, so as to be maintained in substantially the same position, the area which the image surrounding the region of interest occupies moves. That is to say, a field of view of an image, with respect to the region of interest, changes as the region of interest 100 moves, in order to maintain the region of interest in substantially the same position (i.e. when viewed by a user).

For the sake of explanation, a field of view of an image may be considered to be representative of the size, position and/or orientation of the image with respect to the region of interest. Put another way, a field of view of an image may be the relative field of view of an image based on the region of interest. Put yet another way, a field of view of an image defines the amount and position of the area around the region of interest shown by an image.

Thus, in a stabilisation procedure, as the position of the region of interest moves with respect to the ultrasound imaging acquisition device, so the position of the field of view of the image moves. In a further example, as the orientation of the region of interest changes, so the orientation of the field of view (of the image) changes.

The field of view of an image may be determined based on stabilisation information for stabilising the region of interest. Thus, if the current image 210 is stabilised with respect to the previous image 220, the field of view of the current image 210 is different to the field of view of the previous image.

A field of view of an ultrasound image may, for example, be represented by a solid angle detected or sensed by an ultrasound imaging acquisition device. The magnitude of the field of view of the current image may be fixed (a magnitude of 45°), but may have a varying orientation or position with respect to the region of interest. By way of example, when a region of interest is in a first position, the field of view may be ±22.5° from the centre of the region of interest. When the region of interest is in a second position, the field of view may instead range from −5° to +40°.

Referring back to FIGS. 1 and 2, it is understood that the position of the region of interest has moved with respect to the ultrasound image acquisition device (from the previous image to the current image). Accordingly, as a result of stabilizing the region of interest, the field of view of the current image has moved.

The current image may be stabilised based on stabilisation information. Such stabilisation information indicates a motion of the region of interest in the ultrasound sequence (i.e. motion of the region of interest from the previous image to the current image). The stabilisation information may, for example, be a vector (representing movement) or be data indicating a direction and magnitude of a movement.

In some other or further embodiments, the stabilisation information comprises data identifying a field of view of at least one image. The field of view may be defined by identifying data of an image (e.g. data identifying a size, shape, relative position, orientation etc. of the field of view of an image). Thus, an image may be associated with data identifying the field of view of the image (and potentially acting as stabilisation information of the image).

As the field of view of the image moves during stabilisation, if a current image were to be continually presented to a user of the ultrasound system, they would perceive a stationary region of interest with moving borders, as the image updates. Observing this movement of borders may be distracting and increase the difficulty of perceiving the region of interest.

Figure 3:
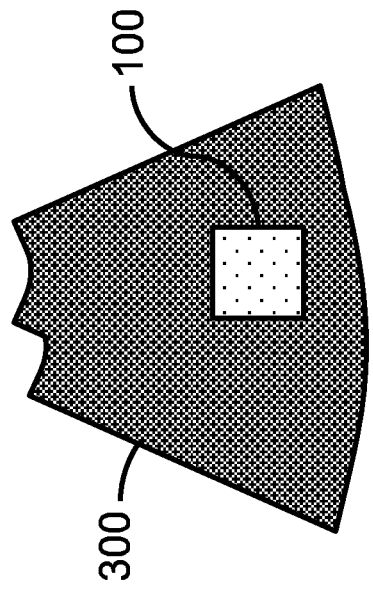
FIG. 3 illustrates a combined image generated based on the current image and the previous image.

With further reference now to FIGS. 3 and 4, a basic concept and method of the invention, in which a composite image is generated, may be understood.

According to one method, a combined image 300 may be generated based on the previous image 120, 220, the current image 110, 210 and stabilization information. The combined image 300 comprises a stabilised region of interest 100, which is determined based on the stabilization information. The field of view of the composite image 300 (i.e. the extent to which the image shows the area surrounding the stabilised region of interest) is the composite of the field of view of the current image 110, 210 and the previous image 120, 220.

Put another way, the field of view of the combined image 300 includes the entire area shown by the previous and current image together. This may be understood to be the union of the field of view of the current image and the field of view of the previous image.

The combined image 300 may thereby be larger than either the previous image or the current image alone. Thus, the number of pixels in the combined image may be greater than the number of pixels in the current image. Furthermore, the shape of the combined image 300 may be different than either the previous or the current image. The difference in size of the combined image may be representative of the movement of the region of interest, and may, in embodiments, be determined based on stabilisation information.

The combined image may be generated, for example, by taking an average pixel value for pixels that overlap one another. In other examples, the most temporally recent value (i.e. values from the current image rather than the previous image) are given priority.

In other words, image data for the combined image may be generated based on image data for the current image and image data for the previous image. Simply by way of example, the current image may be stacked on top of the previous image, and the stack may be merged.

Now with particular reference to FIG. 4, a step of generating a composite image 400, having predetermined dimensions, based on the combined image. The composite image may be of a fixed size and shape, preferably wherein the size of the composite image is greater than the size of the current image 110.

The composite image 400 is formed from at least the combined image 300. That is to say, pixel values of pixels of the composite image are replaced with respective pixel values of pixels of the combined image 300. The remaining area 401 of the composite image (i.e. that area not filled in with the combined image or otherwise assigned with pixel values) may be filled out with a predetermined colour or shade (e.g. grey) or may be filled out based on a predetermined algorithm.

Put yet another way, image data for the composite image 400 may be based on the combined image 300.

As will be apparent, the field of view of the composite image 400 is different to the field of view of the current image 110 alone (and possibly of the combined image 300). As such, there may be areas outside the field of view of the combined image 300 for which the composite image does not comprise any data.

The composite image 400 may be formed by positioning the combined image 300 such that the region of interest 100 lies at a predetermined position (e.g. in the centre of the composite image 400).

Figure 5:
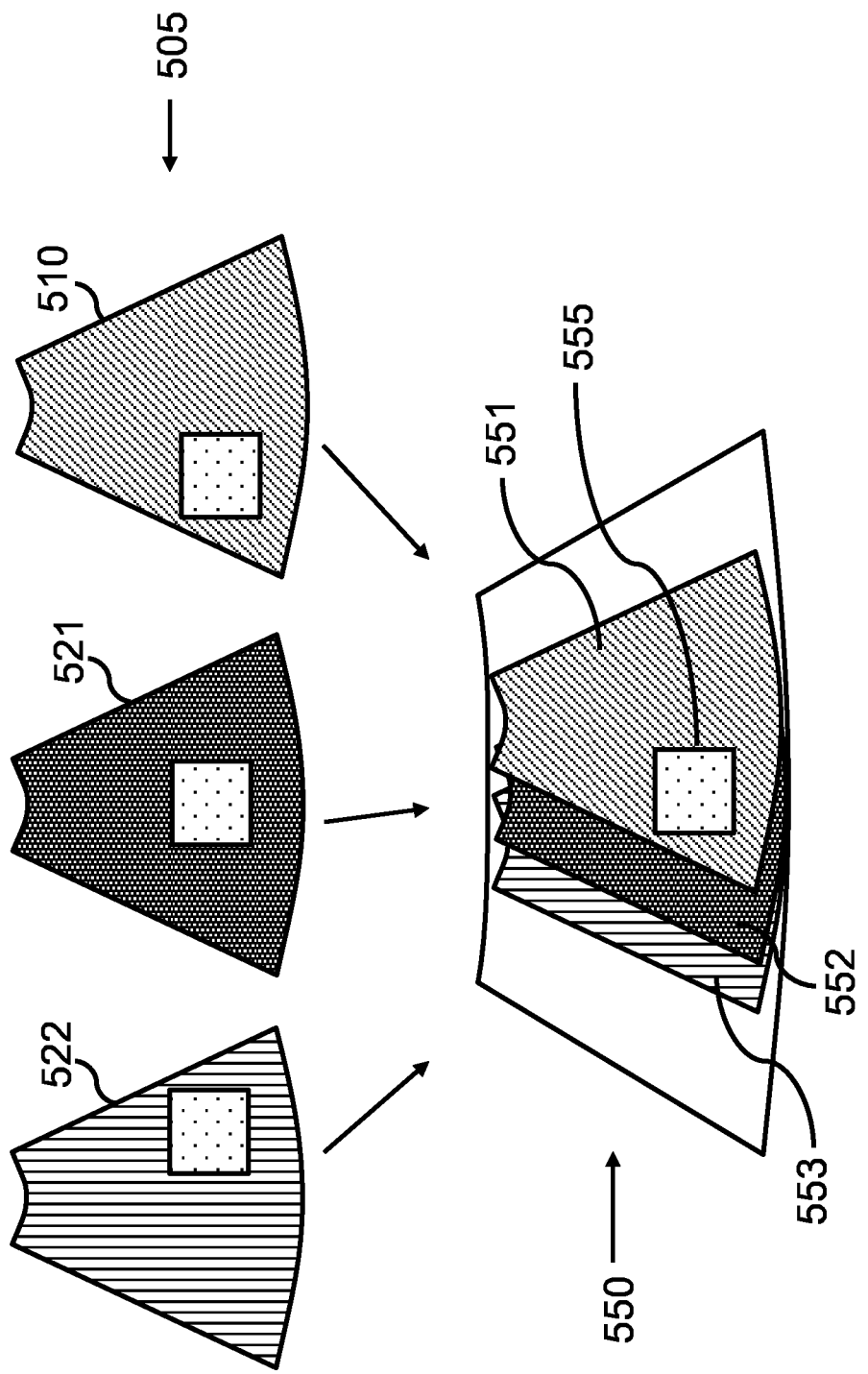
FIG. 5 illustrates a method of generating a composite image based on a current image and two previous images according to an embodiment.

With reference now to FIG. 5, another embodiment a method according to the inventive concept may be understood. The present embodiment illustrates an example in which the intermediate step of creating a combined image need not be performed.

There is shown a sequence 505 of three ultrasound images comprising a current image 510, a first previous image 521 and a second previous image 522. In the present embodiment, the second previous image 522 is more previous (i.e. more temporally distant) than the first previous image 521.

The method comprises generating a composite image 550 based on the current image 510 and the previous images 521, 522. The composite image 550 comprises a stabilised region of interest 555, wherein the stabilisation of the region of interest is based on obtained stabilisation information.

The stabilisation information is information or data suitable for compensating a motion of the region of interest 100 in the sequence 505 of ultrasound images.

By way of example, the stabilisation information may comprise one or more vectors indicating a motion of the region of interest from image to image. For example, the stabilisation information may comprise a first vector representing a motion of the region of interest from the second previous image 522 to the first previous image 521, and a second vector representing a motion of the region of interest form the first previous image 521 to the current image 510.

In this way, each image in the image sequence may be stabilised with respect to the region of interest, such that each image may be associated with a different field of view and thereby a different portion of the composite image.

Generating the composite image may comprise setting pixel values of the composite image based on the current image and at least one previous image.

As the field of view of the current image 510 and the previous images 521, 522 are different (due to stabilization), each image covers, shows or reveals different areas in the vicinity of the region of interest. Whilst these areas may overlap to some extent, some portions of the area may not overlap with another image.

By way of example, pixel values of the composite image lying within the field of view of the current image may be set to the pixel values of the current image. Pixel values of the composite image lying outside the field of view of the current image may be set to pixel values of the at least one previous image.

Preferably, the pixel values of the composite image are set to the most temporally recent (i.e. the closest in time) available pixel value from the current image and the at least one previous image.

In other words, pixel values for the composite image 550 are obtained firstly from the current image 510, then, for remaining pixels, from the first previous image 521, then, for the remaining pixels, from the second previous image 522 and so on.

Pixel data of the composite image may therefore be selected from the temporally closest pixel of the ultrasound sequence.

Pixel values for different areas of the composite image 550 may thereby be determined based on the current image 510 and the at least one previous image 521, 522.

By way of example, a first area 551 may be determined solely based on the current image (i.e. the most temporally recent image). The field of view of the first area 551 corresponds to the field of view of the current image. In other words, the first area 551 shows a region of a same size, location and orientation about the region of interest as the current image 510.

A second area 552, lying outside the field of view of the first area 551 may be determined solely based on the first previous image 521 (i.e. the second most temporally recent image). In other words, pixel values from the first previous image 521 which lie outside the field of view of the current image 510 are assigned to the associated pixels of the composite image 550. The field of view of the second area may be of a different size and shape to the field of view of the first area 551.

A third area 553, lying outside the field of view of both the first area 551 and the second area 552 may be determined solely based on the second previous image 522 (i.e. the third most temporally recent image). In other words, pixels values from the second previous image 522, which lie outside the field of view of both the current image and the first previous image are assigned to the associated pixels of the composite image 550.

The composite image may be thought to comprise the union combination of the current image and the at least one previous image, with priority (i.e. preference in a stacking order) given to temporally closer images. In other words, the current image and the previous images may be stitched or composited together so as to form a portion of the composite image.

In an embodiment, the composite image is processed in accordance with a smoothing algorithm. The smoothing algorithm may be adapted to smooth across the borders of at least the first area (i.e. the field of view associated with the current image).

The composite image may be processed in accordance with a filling algorithm adapted to fill out the unassigned pixels of the composite image according to a predetermined method. By way of example, such an algorithm may select the nearest available pixel value (e.g. a pixel value from the current/previous image(s)) or may average the currently assigned pixel values of the composite image.

The stabilisation information may be obtained by tracking the region of interest throughout the ultrasound sequence. Tracking of the region of interest may be performed using surrounding image features of the region of interest. In particular, the tracking of the region of interest may be performed using an algorithm titled "Sparse Demons": O. Somphone et al., "Fast myocardial motion and strain estimation in 3D cardiac ultrasound with Sparse Demons," 2013 IEEE 10th International Symposium on Biomedical Imaging, San Francisco, Calif., 2013, pp. 1182-1185.

The output of this algorithm "Sparse Demons" is a translation vector, optimized so that the global motion of the region of interest is compensated.

As the region of interest is stabilised in the composite image (i.e. kept in a substantially same location), the stabilisation information may define a position of the current image and/or the at least one previous image with respect to one another. In other words, the stabilisation information may indicate a field of view of each image with respect to the region of interest (and thereby the composite image).

The method may comprise identifying the region of interest (e.g. for tracking purposes). In examples, the region of interest is identified by a segmentation step, which may exist in an ultrasound application workflow or an interactive step, where the user draws a box around the region of interest (on a displayed image) or otherwise identifies the region of interest (e.g. inputting co-ordinates of the location of the region of interest).

Figure 6:
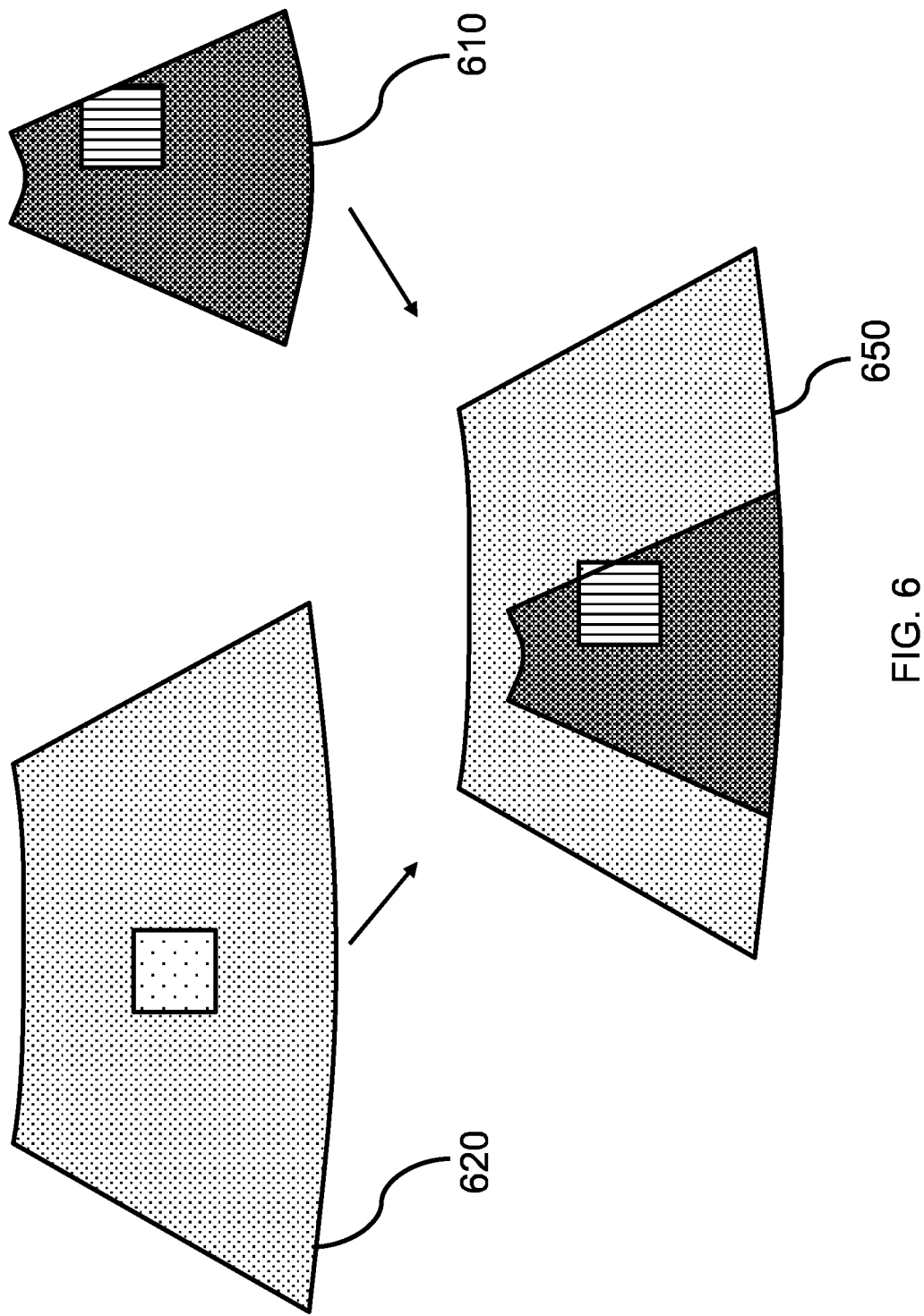
FIG. 6 illustrates a method of generating a composite image based on a current image and a previous composite image according to another embodiment.

With reference now to FIG. 6, a further or other embodiment of a method according the inventive concept may be understood. In the embodiment illustrated by FIG. 6, the at least one previous image comprises a previous composite image 620.

The previous composite image 620 may, for example, have been generated in a previous composite image generation step. In this way, the sequence of ultrasound images may, in some embodiments, comprise a previous composite image and a current image.

The method comprises obtaining stabilisation information for compensating a motion of the region of interest.

In some embodiments, the stabilisation information identifies a field of view of at least the current image 610 with respect to the field of view of the (previous) composite image. By way of example, in the event that the composite image has a field of view ranging from −45° to +45° (with respect to the centre of the region of interest), a current image may have a field of view ranging from −25° to +10° (with respect to the centre of the region of interest).

In other embodiments, the stabilisation information identifies a vector movement of the region of interest (e.g. from a position in the composite image to an updated position in the current image).

The method comprises generating a composite image 650 by replacing a number of pixel values of the previous composite image 620 with pixel values from the current image 610. This may be performed based on the stabilisation information (i.e. to identify where the field of view of the current image lies within the field of view of the previous composite image).

As the current image contains the region of interest, it is apparent that the composite image comprises a stabilised region of interest, such stabilisation being based on the stabilisation information. In this way, the region of interest in the composite image may be stabilised, such that the region of interest remains in substantially the same position when the previous composite image 620 is updated based on the current image 610. Thus, the stabilisation of the region of interest is based on at least the stabilisation information.

Pixels of the previous composite image 620 that fall within the field of view of the current image 610 are replaced with the associated pixel values of the current image 610. Pixel values of the current image 610 that fall outside of the field of view of the previous composite image may be discarded.

In this way, a previous composite image 620 may be updated with new data from a current image 610 based on at least the stabilisation data. The new data preferably includes at least the region of interest, such that the region of interest of the composite image 650 is stabilised based on the stabilisation information. An advantage of this approach may be that a user is provided with a real-time update on the most relevant diagnostic information originating from the vicinity of the region of interest (comprised in the current image 610), while a computing power of an ultrasound system can be saved by keeping the rest of the pixels in the composite image 650 the same as in the previous composite image 620.

In other words, the method comprises generating a composite image 650 based on a current image 610 and at least one previous image (here: previous composite image 620). A region of interest in the composite image is stabilised based on stabilisation information, as the stabilisation information defines or directs where the current image 610 is to be positioned in the new composite image 650.

Figure 7:
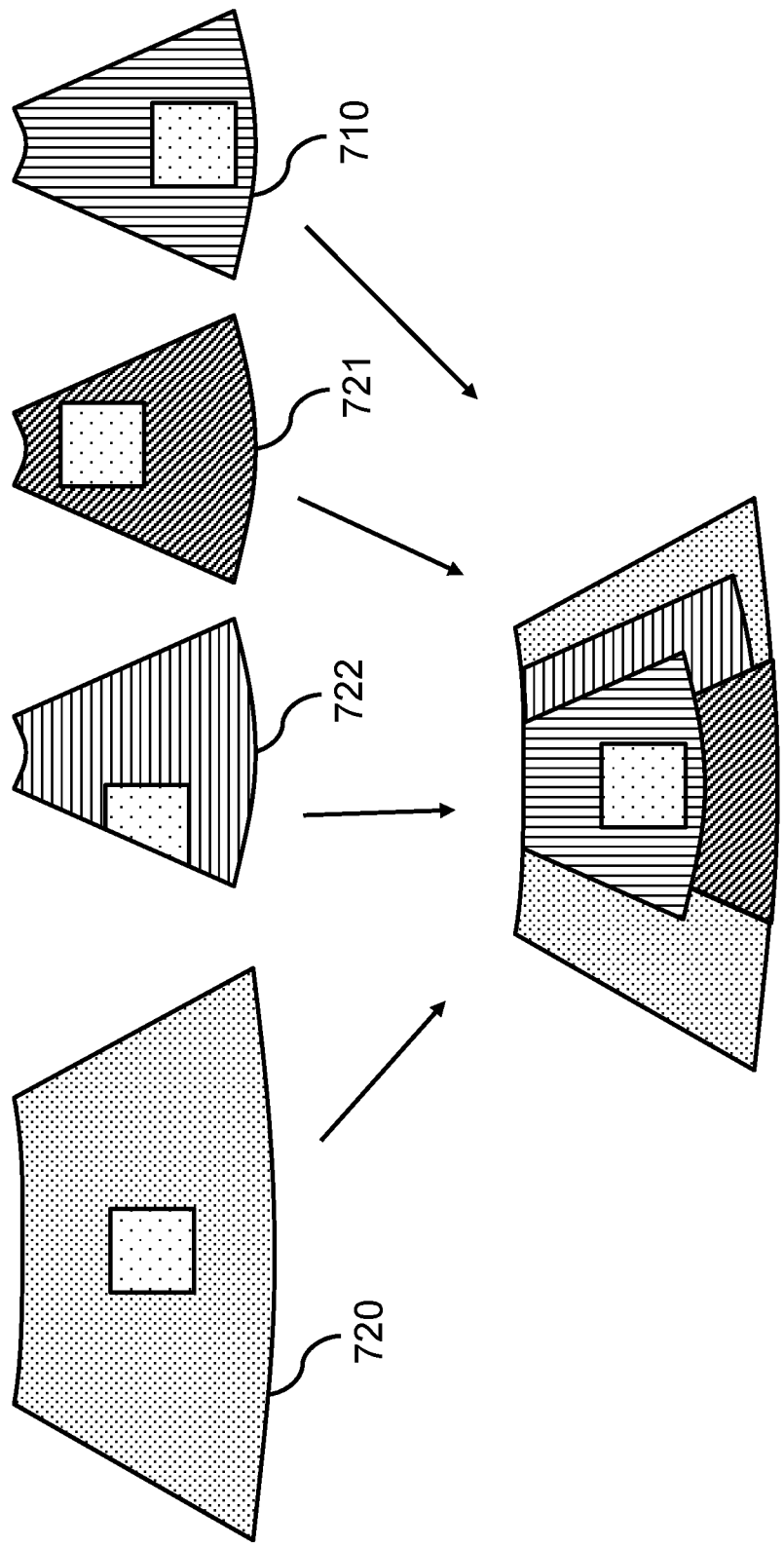
FIG. 7 illustrates a method of generating a composite image based on a current image and at least one previous composite image, according to yet another embodiment.

In a method according to yet another embodiment, which will be hereafter elucidated with reference to FIG. 7, the at least one previous image comprises a previous composite image 720, a current image 710, a first previous image 721 and a second previous image 722.

As in previously described embodiments, the first previous image is less temporally recent than the current image 710, but more temporally recent than both the second previous image 722 and the previous composite image 720. In other words, the current image 710 is later in an ultrasound image sequence in comparison to the previous images.

The method comprises replacing the pixel values of pixels of the previous composite image 720 that fall or lie within the field of view of the current image 710 by the associated pixel values of the current image 710.

The method further comprises replacing the pixel values of pixels of the previous composite image 720 that fall or lie within the field of view of the first previous image 721, but outside the field of view of the current image 710, by the associated pixels values of the first previous image 721.

The method yet further comprises replacing the pixel values of pixels of the previous composite image 720 that fall or lie within the field of view of the second previous image 722, but outside the field of view of the current image 710 and the first previous image 721, by the associated pixels values of the second previous image 722.

In other words, in the above described embodiment, the method comprises updating the previous composite image 720 with pixel data from a plurality of ultrasound images in an ultrasound sequence. Priority is given to more recent images over less recent images. In this way, if more than one image occupies a particular area, the most temporally recent image is given priority. The advantage of this approach also lies in the reduced computing power requirements of the ultrasound system, whilst providing a real-time diagnostic imaging information to the user. This is especially suitable in application of portable ultrasound systems with specific limitations on consumed power.

Put yet another way, the method comprises replacing pixels of the previous composite image 720 that fall within the field of view of the current image 710 by the pixels of the current image 710. The pixel values of pixels that fall outside the field of view of the current image 710 are replaced by the temporally closest value (i.e. the most recent available value for equivalent pixels).

Described embodiments may thereby allow a buffer of ultrasound images to be generated. Although the above described example uses only two previous images in generating the composite image, it will be apparent that any number of previous images may be used to advantage. In preferable embodiments, no more than five previous images are used to generate the composite image.

Using a buffer of previous images, rather than updating with each newly generated current image, reduces an amount of processing power required to carry out the method. Furthermore, use of a buffer in this manner may be preferable to allow the user to have an increased focus on the region of interest with a reduced number of distractions (e.g. from an updating image).

The composite image may be processed in accordance with a smoothing algorithm. The smoothing algorithm may be adapted to smooth a boundary between replaced pixels and un-replaced pixels in the composite image. In further or other embodiments, the smoothing algorithm smooths a boundary between areas replaced by pixels from different images of the ultrasound sequence (e.g. between a first area replaced by pixels from the current image and a second area replaced by pixels from the first previous image).

In other words, the current image and the at least one previous image may be processed in accordance with a smoothing algorithm.

In aforementioned embodiments, known smoothing algorithms may be used, for example, Gaussian functions, exponential smoothing algorithms, Savitzky-Golay filters and so on.

Use of a smoothing algorithm may reduce artifacts in the composite image that detract a user's attention from the region of interest.

The present inventive concept recognises that if an ultrasound imaging acquisition device is fixed in position, the motion of a region of interest is typically periodic or substantially periodic. As such, the size and shape of the composite image may be determined in advance, as the overall motion of the region of interest may be predicted with a suitable level of accuracy.

In previously described embodiments, the predetermined dimensions of the composite image may be calculated based on a composite image previously built up over time. By way of example, a composite image may be formed by stitching or compositing a sequence of stabilised ultrasound images together. As movement of a region of interest is considered to be substantially periodic, as more and more ultrasound images are composited together, a composite image having substantially fixed dimensions is generated.

Purely by way of example, if the combined image of FIG. 3 were to be combined with further images (taken by the ultrasound system), a final combined image would be produced having a substantially unchanging overall field of view. The overall field of view of this final combined image may be used as the field of view (i.e. predetermined dimensions) of the composite image.

A method according to an embodiment may comprise determining the overall field of view of the composite image, defining the area around the region of interest which is made visible or shown by the composite image. The size of the overall field of view corresponds to the predetermined dimensions of the composite image.

Alternatively, the predetermined dimensions of the composite image may be based on user input (e.g. defining a desired predetermined dimension of the composite image) or information received from a sensor (e.g. adapted to measure a size of a patient etc.) In yet other embodiments, the predetermined dimensions of the composite image may be determined based on information about the region of interest (e.g. a size or location of the region of interest). In some embodiments, the larger the region of interest, the larger the size of the composite image.

In some embodiments, the method comprises determining the number of previous images to use in generating the composite image. In preferable embodiments, the number of previous images is calculated based on period of motion of the region of interest. In particular, it is preferable that the number of previous images covers at least one period of motion (i.e. one oscillation) of the region of interest.

Alternatively, the number of previous images may be predetermined (e.g. no more than five or no more than ten) or may be determined based on a received user input.

In preferred embodiments, there is a 3D ultrasound method for stabilising a region of interest. Such embodiments may be as previously described, wherein a change in field of view represents translation and/or change of shape due to out of plane motion. As such a movement in more than one plane causes a change in the field of view. For example, a downward movement of a region of interest causes a change in the field of view.

In some conceivable embodiments, only the region of interest is updated in response to a current image. In an example, based on the stabilisation information, the region of interest in a current image is identified and pixel values of a previous composite image (showing a previous instance of the region of interest) are updated based on the current image. Such embodiments may be preferable when only a low processing power is available (as this will significantly reduce the workload of a processor carrying out the method).

In above described embodiments, a current image may be understood to be an image most recently output or currently being output by an ultrasound image acquisition device. A previous image may be understood to comprise either a previous composite image or images previously output by the ultrasound image acquisition device. In other words, a previous image is produced earlier in time than a current image.

Whilst methods according to embodiments are preferably performed in real-time, such that a current image is an image immediately generated by an ultrasound system, it will be apparent that the method may be applied to a stored sequence of ultrasound images, where a current image is a selected image from the sequence of ultrasound images. Concepts of the present invention may therefore be applied in both an online and offline scenario.

Figure 8:
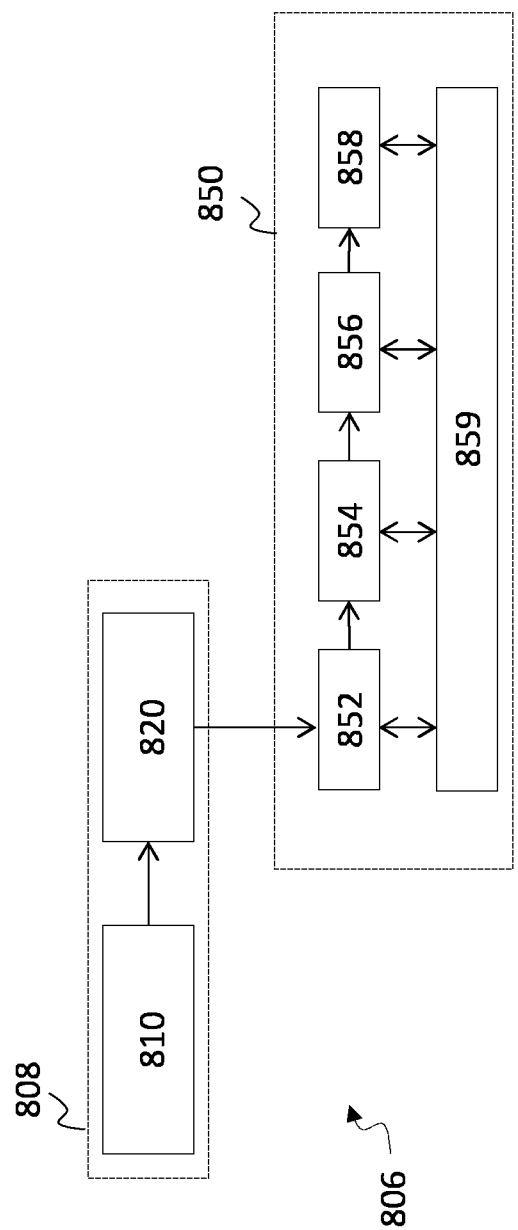
FIG. 8 illustrates an ultrasound system according to an embodiment.
Figure 9:
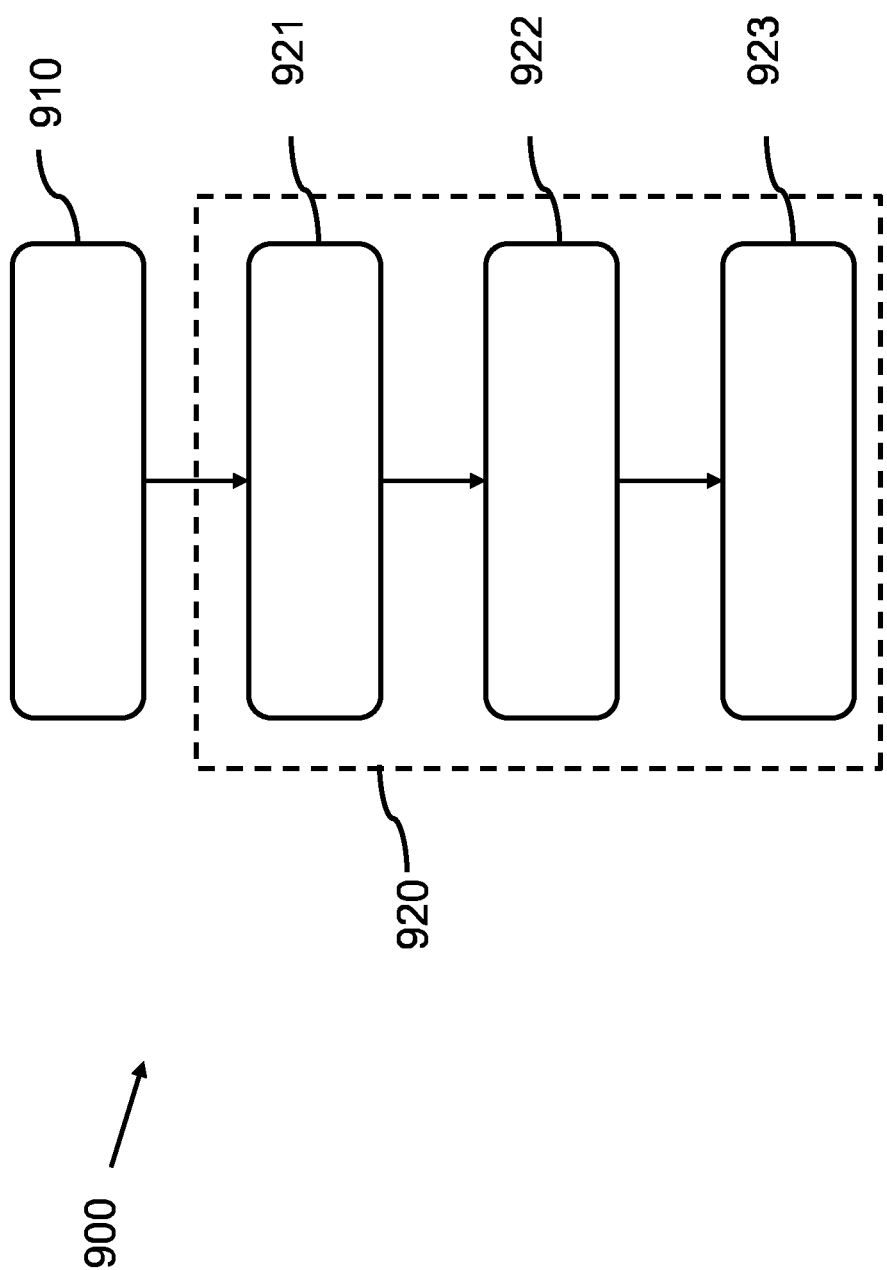
FIG. 9 is a flow chart illustrating a method according to an embodiment.

According to one aspect of the invention, a schematic illustration of which is provided in FIG. 8, there is provided an ultrasound system 806, comprising an ultrasound image acquisition unit 808 and an ultrasound imaging system 850. The ultrasound image acquisition unit 808 comprises an ultrasound transducer array 810, for example mounted in an ultrasound probe, for transmitting ultrasonic waves and receiving echo information. In examples, the transducer array may alternatively comprise piezoelectric transducer elements formed of materials such as PZT, CMUT or PVDF. The transducer array may be a one or two-dimensional array of transducer elements capable of scanning in three dimensions to generate 3D image data of a volume of interest (scanned volume).

In addition to the ultrasound probe, a signal processing unit 820 may be provided as part of the ultrasound image acquisition unit 808 to process received echo data and form 3D image data which may then be provided to the ultrasound imaging system 850 for processing. The signal processing unit may be located within the ultrasound probe.

In embodiments, the ultrasound imaging system 850 comprises a region of interest identifier 852 adapted to identify a region of interest in a current image based on the image data provided by the image acquisition unit 808.

The ultrasound imaging system 850 may comprise an image stabiliser 854 adapted to obtain stabilization information for compensating a motion of a region of interest within the scanned volume. The stabilization information may be obtained based on the identified region of interest (ROI) and at least one previous image (for example). This can be achieved by tracking a location of the ROI in the image data corresponding to the current image and at least one previous image.

In further embodiments, the ultrasound imaging system 850 comprises a field of view obtaining system 856 adapted to obtain data indicative of a field of view of each image in the image sequence.

The ultrasound imaging system 850 comprises an image generator 858 adapted to generate a composite image of the current image and the at least one previous image, such as previously described. The image generator may, in some embodiments, be adapted to generate a composite image of a previous composite image and the current image. Put another way, the image generator may update a previously generated composite image with pixel data from one or more ultrasound images in an ultrasound sequence, the one or more ultrasound images being more temporally recent than the previously generated composite image.

The ultrasound imaging system 850 may comprise a memory system 859 adapted to store at least one previous image. Thus, the memory system 859 may act as a buffer for storing at least a portion of a sequence of ultrasound images.

The ultrasound imaging system 850 may communicate with a display (not shown) which is adapted to visually display the composite image. Such a display may, for example, comprise an LED or LCD screen and may, for example, be touch-sensitive.

As will be apparent from the foregoing description, there is provided an ultrasound imaging method 900 for stabilising a region of interest. The method 900 comprises obtaining 910 stabilisation information for compensating motion of a region of interest in a sequence of ultrasound images. The method further comprises generating 920 a composite image based on a present image and at least one previous image of the ultrasound sequence. The generating 920 may comprise stabilising 921 the region of interest in the current image based on stabilization data, generating 922 the composite image by compositing the stabilized current image with at least one previous image and processing 923 image data of the current image and the at least one previous image in accordance with a smoothing algorithm, The present invention may be embodied as a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fibre-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibres, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging method for stabilizing a region of interest, the method comprising:
   receiving a sequence of ultrasound images, the sequence of ultrasound images comprising a current image and at least one previous image, wherein the current image has a current field of view and the at least one previous image has a previous field of view, the previous field of view being different from the current field of view;
   obtaining stabilization information for compensating motion of a region of interest in the sequence of ultrasound images, wherein the region of interest comprises less than an entirety of the current image and the at least one previous image;
   determining an overall field of view for a composite image to be generated using the current image and the at least one previous image, wherein the overall field of view comprises a union of the previous field of view and at least a portion of the current field of view, and wherein the overall field of view has predetermined dimensions larger than dimensions of the current image;
   based on the stabilization information and using the current image and the at least one previous image, generating the composite image having the overall field of view, wherein the region of interest is placed at a predetermined and fixed position within the composite image, by:
   determining pixel values for the composite image using pixel values of the current image, for portions of the current image that fall within the overall field of view of the composite image;
   discarding pixel values of the current image that fall outside the overall field of view of the composite image; and
   determining pixel values for the composite image using pixel values of the at least one previous image for portions of the composite image that do not overlap with the current image.

2. The method of claim 1, further comprising determining the overall field of view of the composite image based on at least one previous composite image.

3. The method of claim 1, wherein the generating the composite image comprises using a predetermined color or predetermined algorithm to assign pixel values to pixels of the composite image outside the current field of view and the previous field of view.

4. The method of claim 1, further comprising processing image data of the current image and the at least one previous image in accordance with a smoothing algorithm.

5. The method of claim 1, wherein the obtaining stabilization information comprises:
   determining a location of the region of interest in the current ultrasound image;
   determining a location of the region of interest in an immediately previous ultrasound image from the at least one previous image; and
   determining a change in location of the region of interest from the immediately previous ultrasound image to the current ultrasound image to generate the stabilization information.

6. The method of claim 1, wherein the stabilization information comprises a vector indicative of a relative translation of the region of interest in the current ultrasound image with respect to an immediately previous ultrasound image.

7. The method of claim 1, wherein the generating the composite image is based on the current image and no more than five previous images from the at least one previous image.

8. The method of claim 1, further comprising obtaining an identification of the region of interest in the current image, and wherein the identification of the region of interest is performed by either receiving a user input indicative of the region of interest or performing a segmentation of image data of an ultrasound system.

9. The method of claim 1, wherein the method is a 3D ultrasound imaging method and the stabilization information is for compensating a 3D motion of the region of interest in a sequence of 3D ultrasound images.

10. The method of claim 1, wherein the predetermined dimensions are based on a user input.

11. The method of claim 1, wherein the predetermined dimensions are based on at least one of a size or location of the region of interest.

12. The ultrasound imaging method of claim 1, wherein each of the current field of view, the previous field of view, and the overall field of view are defined based on at least one of dimensions, shape, size, position, or orientation of a depicted or imaged area relative to the region of interest.

13. An ultrasound imaging system comprising:
   a non-transitory computer readable medium encoded with computer-readable program instructions; and
   at least one processor configured to execute the computer-readable program instructions, which when executed, receives a sequence of ultrasound images, the sequence of ultrasound images comprising a current image and at least one previous image, wherein the current image has a current field of view and the at least one previous image has a previous field of view, the previous field of view being different from the current field of view;

obtains stabilization information for compensating motion of a region of interest in the sequence of ultrasound images, wherein the region of interest comprises less than an entirety of the current image and the at least one previous image;

determines an overall field of view for a composite image to be generated using the current image and the at least one previous image, wherein the overall field of view comprises a union of the previous field of view and at least a portion of the current field of view, and wherein the overall field of view has predetermined dimensions larger than dimensions of the current image;

based on the stabilization information and using the current image and the at least one previous image, generates the composite image having the overall field of view, wherein the region of interest is placed at a predetermined and fixed position within the composite image;

determines pixel values for the composite image using pixel values of the current image, for portions of the current image that fall within the overall field of view of the composite image;

discards pixel values of the current image that fall outside the overall field of view of the composite image; and determines pixel values for the composite image using pixel values of the at least one previous image for portions of the composite image that do not overlap with the current image.

14. The ultrasound imaging system of claim 13, wherein the at least one processor configured to execute the computer-readable program instructions, which when executed, further identifies the region of interest in at least the current image.

15. The ultrasound imaging system of claim 13, wherein the at least one previous image comprises at least one previous composite image comprising the region of interest.

16. The ultrasound imaging system of claim 13, further comprising a sensor, wherein the predetermined dimensions are based on information received from the sensor.

* * * * *